United States Patent [19]
Murray

[11] Patent Number: 5,797,678
[45] Date of Patent: Aug. 25, 1998

[54] BONE CEMENT MIXING DEVICE AND METHOD

[76] Inventor: William M. Murray, 5020 Ritter Rd., Suite 211, Mechanicsburg, Pa. 17055-4837

[21] Appl. No.: 533,171

[22] Filed: Sep. 25, 1995

[51] Int. Cl.⁶ .................................................. B01F 13/06
[52] U.S. Cl. ........................ 366/139; 366/139; 366/197
[58] Field of Search ................................ 366/139, 197, 366/279, 204, 207, 241, 244, 247, 281, 191, 189, 194; 422/99, 225

[56] References Cited

U.S. PATENT DOCUMENTS

| | | |
|---|---|---|
| 277,250 | 5/1883 | Espel . |
| 480,714 | 8/1892 | Crozier ................................ 366/204 |
| 735,353 | 8/1903 | Eifert ................................. 366/197 |
| 3,679,184 | 7/1972 | Woodham et al. . |
| 3,937,444 | 2/1976 | Kapp . |
| 3,946,996 | 3/1976 | Gergely . |
| 4,015,945 | 4/1977 | Frankel et al. . |
| 4,020,832 | 5/1977 | Kirkpatrick et al. . |
| 4,277,184 | 7/1981 | Solomon ............................. 366/139 |
| 4,517,888 | 5/1985 | Gould . |
| 4,669,275 | 6/1987 | Ohgushi et al. ..................... 366/189 |
| 4,676,658 | 6/1987 | Herfeld . |
| 4,721,390 | 1/1988 | Lidgren . |
| 4,772,434 | 9/1988 | Myers . |
| 4,854,715 | 8/1989 | Eirich et al. . |
| 4,854,717 | 8/1989 | Crane et al. ......................... 366/197 |
| 4,889,432 | 12/1989 | Patterson . |
| 4,961,647 | 10/1990 | Coutts et al. . |
| 4,973,168 | 11/1990 | Chan . |
| 5,100,241 | 3/1992 | Chan . |
| 5,145,250 | 9/1992 | Planck et al. . |
| 5,265,956 | 11/1993 | Nelson et al. . |
| 5,328,262 | 7/1994 | Lidgren et al. . |
| 5,344,232 | 9/1994 | Nelson et al. . |
| 5,348,391 | 9/1994 | Murray . |
| 5,368,385 | 11/1994 | Adamo et al. . |
| 5,368,386 | 11/1994 | Murray . |
| 5,393,140 | 2/1995 | Blach . |
| 5,395,167 | 3/1995 | Murray . |
| 5,415,474 | 5/1995 | Nelson et al. . |
| 5,549,381 | 8/1996 | Hays et al. .......................... 366/139 |

FOREIGN PATENT DOCUMENTS

WO9310892 6/1993 WIPO .

Primary Examiner—Tony G. Soohoo
Attorney, Agent, or Firm—Webb Ziesenheim Bruening Logsdon Orkin & Hanson, P.C.

[57] ABSTRACT

A device for mixing bone cement of the present invention includes a housing having an open top. An internal chamber is located in the housing. The internal chamber is inclined at an angle from a vertical axis. The device further includes a mixer having stirrer elements extending into the internal chamber and a cap configured to fit over the open top of the housing to sealably close the housing. The method of mixing bone cement according to the present invention includes the steps of placing bone cement powder into an inclined chamber, introducing bone cement liquid into the inclined chamber and then mixing the bone cement liquid and bone powder to form mixed bone cement.

47 Claims, 9 Drawing Sheets

BONE CEMENT MIXING DEVICE AND METHOD

BACKGROUND OF THE INVENTION

1. Field of the Invention

This invention relates generally to a device and method for mixing bone cement and, more particularly, to a device and method for mixing bone cement under vacuum conditions.

2. Description of the Prior Art

Bone cement is prepared by mixing a very fine cement powder, typically polymethylmethacrylate (polymer) with a liquid monomer, typically methylmethacrylate (monomer). The mixed bone cement is used as a grout for implanting prosthetic devices in live bone. Polymer is customarily supplied presterilized in pouches which typically contain 40 grams of powder. Monomer liquid is customarily supplied presterilized, in ampoules, each of which contains 20 milliliter of liquid. Most manufacturers recommend combining powder and liquid in a ratio of 2 g powder to 1 ml liquid. By convention, the quantity of 40 g of polymer powder and 20 ml of monomer liquid is termed "1 dose" of cement.

After initial combination of polymer powder and monomer liquid, the mixture becomes progressively more viscous. Most formulations, when mixed at room temperature, become rigid at 9 to 12 minutes after the start of mixing. Bone cement is mixed in the operating room under sterile conditions and is then transferred directly to a prepared implantation site. During mixing, gas voids or bubbles become trapped in the viscous cement. These voids form hollow inclusions in the cured cement which weaken the bone cement and increase the possibility of cement fracture and resultant loosening of an implanted prosthetic device.

In order to minimize the formation of trapped gas bubbles during mixing of the bone cement, devices for mixing the bone cement under vacuum conditions have been developed. In these devices, bone cement is mixed by placing the fine polymer powder and monomer liquid into an interior mixing chamber, closing the device and connecting the device to a vacuum source. When the mixing device is closed, the vacuum source reduces the pressure within the closed mixing chamber and draws the relatively large volume of air from between the very fine dry particles of powdered polymer out of the mixing chamber. A mixer is manually operated to mix the polymer and monomer to form bone cement.

These vacuum mixing devices can generally be categorized as either in-bowl or in-syringe devices. In the in-bowl mixing devices, the polymer powder and monomer liquid are mixed in a mixing bowl, the width of which is greater than the depth of the material. It is not technically difficult to mix cement in a bowl, and with some representative devices, the order in which materials are dispensed into the bowl before mixing makes little difference. However, in most cases, it is required that cement be injected from a syringe into the implantation site thus necessitating the additional step of transferring mixed cement from the bowl to the syringe. Unfortunately, transfer of the bone cement mixture from the mixing bowl to the injection syringe has a tendency to reintroduce air bubbles into the bone cement mixture. Further, significant time can be required for transfer of viscous bone cement mixture from the bowl to the syringe which reduces the remaining working time available for implantation of the cement and also results in increased viscosity of the cement at the time that it becomes available to the surgeon. Additionally, in-bowl mixing is wasteful of the bone cement since a certain amount of the mixed bone cement will adhere to the bowl thus reducing the amount available for transfer to the syringe and injection into the implantation site. Finally, since bowls used for mixing cement are usually discarded after use, using this type of device consumes more materials than in using in-syringe devices described hereinbelow. U.S. Pat. Nos. 4,015,945 to Frankel et al. and 4,961,647 to Coutts et al. are examples of in-bowl mixing devices.

In order to overcome the problems associated with the in-bowl mixing devices, in-syringe mixing devices have been developed in which the bone cement is mixed directly in a vertically oriented syringe body. A funnel is typically attached to the open upper end of the syringe body to facilitate pouring of polymer powder into the syringe and to accommodate the greater volume occupied by powder before it has been wetted by the monomer liquid. After mixing, a nozzle assembly is attached to the syringe body and the mixed bone cement is injected into the implantation site directly from the syringe body. Examples of in-syringe mixing devices are found in U.S. Pat. Nos. 4,721,390; 5,265,956; 5,344,232; and 5,368,386.

However, there are problems associated with these known in-syringe mixing devices in which the length of the syringe body is by necessity significantly greater than its diameter. It is difficult to achieve mixing of monomer liquid and polymer powder which is homogeneous from end to end in the syringe, particularly where more than one dose must be mixed.

If multiple doses of powder are poured into a conventional in-syringe mixer followed by pouring of the same number of doses of monomer liquid, the liquid will rapidly wet the powder across the top of the powder. This will prevent monomer liquid from flowing to the bottom of the syringe because air that would be displaced by downward flow of the liquid cannot escape. After this has happened, no known rotary mixing mechanism can achieve wetting of the powder at the bottom of the syringe much less achieve homogeneous mixing of the powder and monomer liquid throughout the syringe. If multiple doses of liquid are poured first, the powder first contacting the monomer liquid will absorb the liquid, and it will not be possible to wet the rest of the powder at the top of the syringe.

Current practice in using in-syringe devices with rotary mixing mechanisms to mix more than one dose calls for dispensing materials into the syringe by alternating between pouring fractional amounts of monomer liquid and of polymer powder until the total quantity to be mixed has been placed in the syringe. While this procedure can result in a fairly homogeneous mixture, it is time consuming to accomplish. Since the viscosity of bone cement rises continuously from the time of combining the powder and the liquid, use of this procedure inevitably delays the onset of mixing until viscosity has risen appreciably. This reduces the thoroughness of mixing which can be achieved and, in consequence, can compromise the strength of the cement. Whereas this is an appreciable disadvantage in mixing two doses of cement, it is a formidable obstacle in attempting to simultaneously mix three or more doses of cement by the in-syringe method.

Also in the art are in-syringe mixers with a mixing mechanism that includes longitudinal motion. The operation of such mixers is difficult and tiring. Moreover, the time required for adequate mixing is undesirably long resulting in reduced working time for the surgeon and increased viscosity at the time of dispensing. With in-syringe mixers of this type, the user is instructed to add monomer liquid before polymer powder.

With any cement mixing device, it is desirable to be able to pour all of the polymer powder prior to pouring any of the monomer liquid. If the powder may be poured first, then this time-consuming step can be accomplished at any time in advance of the time when the mixed bone cement is required. Since pouring monomer liquid consumes little time, the elapsed time between combining materials and the start of mixing will be at a minimum and, as a consequence, the mixture viscosity will be at a minimum during the mixing process. Minimum viscosity will permit maximum efficiency of mixing. Additionally, the monomer liquid vapor has an odor which some people find objectionable. If monomer liquid is poured only after all the polymer powder has been dispensed, the time during which the operator will be exposed to the monomer vapor will be minimized. After closure of the mixing device for stirring, monomer vapor will no longer escape to the atmosphere. It is common practice to provide filter means in the vacuum conduit for removal of monomer vapor.

Another problem with in-syringe mixing devices in the current art is that polymer powder being dispensed into them has a long free-fall path before coming to rest at the bottom of the mixing chamber. This tends to result in powder falling with sufficient force to cause billowing of polymer dust from the mixing device, with this dust coming to rest on clean materials in the sterile field. This is potentially harmful as the dust is quite abrasive as well as potentially irritating.

A further problem with these conventional in-syringe mixing devices is that they are generally very technique sensitive in that the quality of the mixed bone cement depends heavily upon the mixing technique of the person preparing the bone cement. Thus, the quality of the mixed bone cement varies greatly between different preparers.

Therefore, it is an object of the invention to provide a bone cement mixing device which provides rapid, thorough and reproducible mixing of bone cement under vacuum in a syringe. Another object is to provide a device in which all the required polymer powder may be placed into the mixing chamber before addition of any monomer liquid. An additional object is to provide means for minimizing the billowing of polymer powder from the mixing device while the powder is being poured into the mixing device.

SUMMARY OF THE INVENTION

A device for mixing bone cement of the present invention includes a housing having an open top. An internal chamber is located in the housing. The internal chamber is inclined at an angle from a vertical axis. The device further includes a mixer having stirrer elements extending into the internal chamber and a cap configured to fit over the open top of the housing so as to sealably close the housing.

The method of mixing bone cement according to the present invention includes the steps of placing bone cement powder into an inclined chamber, introducing bone cement liquid into the inclined chamber and then mixing the bone cement liquid and bone cement powder to form mixed bone cement.

A complete understanding of the invention will be obtained from the following description when taken in connection with accompanying drawing figures wherein like reference characters identify like parts throughout.

DESCRIPTION OF THE PREFERRED EMBODIMENTS

While the embodiments described hereinbelow are primarily intended for mixing up to three doses of bone cement, it should be understood that the present invention is not limited in applicability to this particular size.

Figure 1:
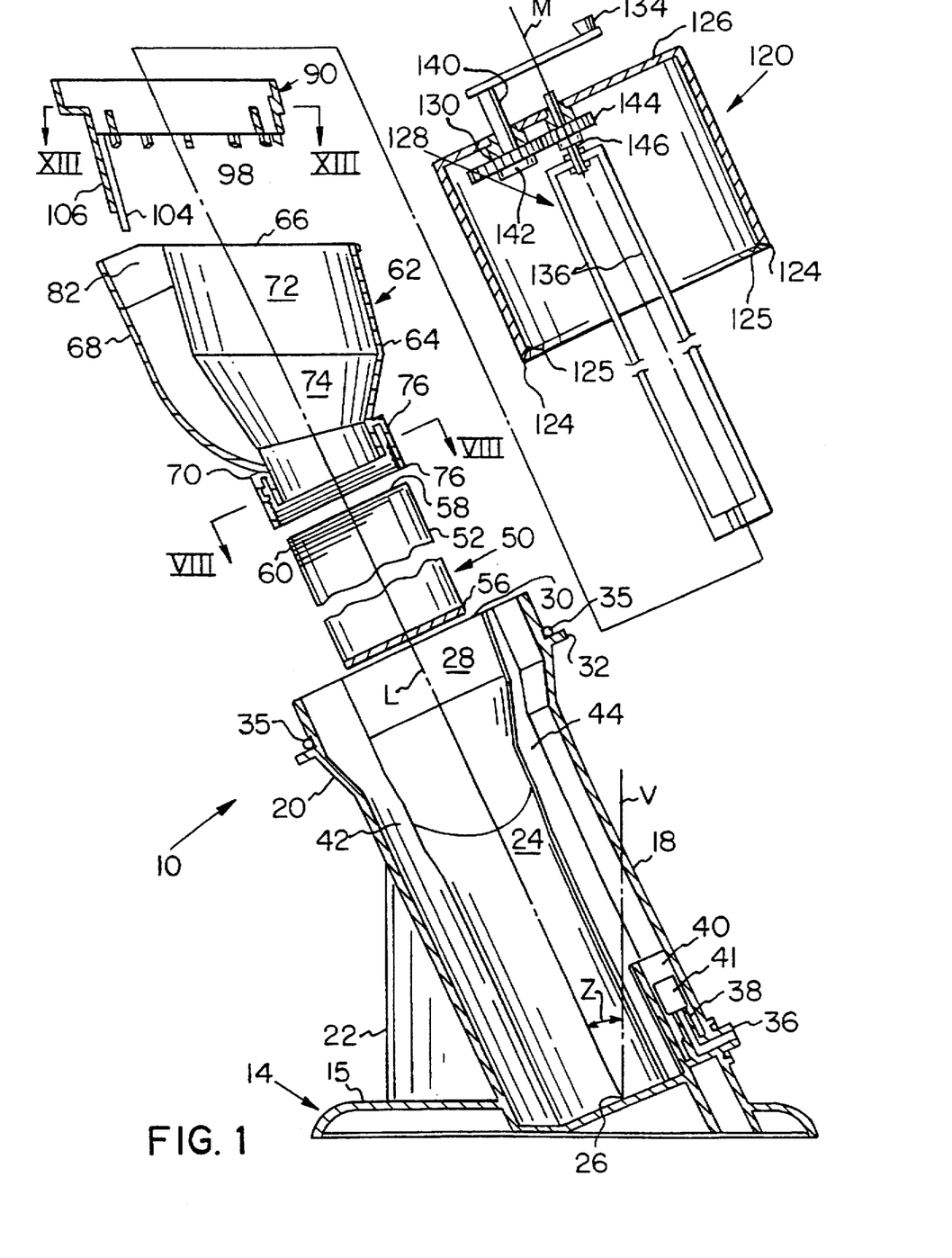
FIG. 1 is an expanded, sectional view of a first embodiment of the bone cement mixing device.
Figure 2:
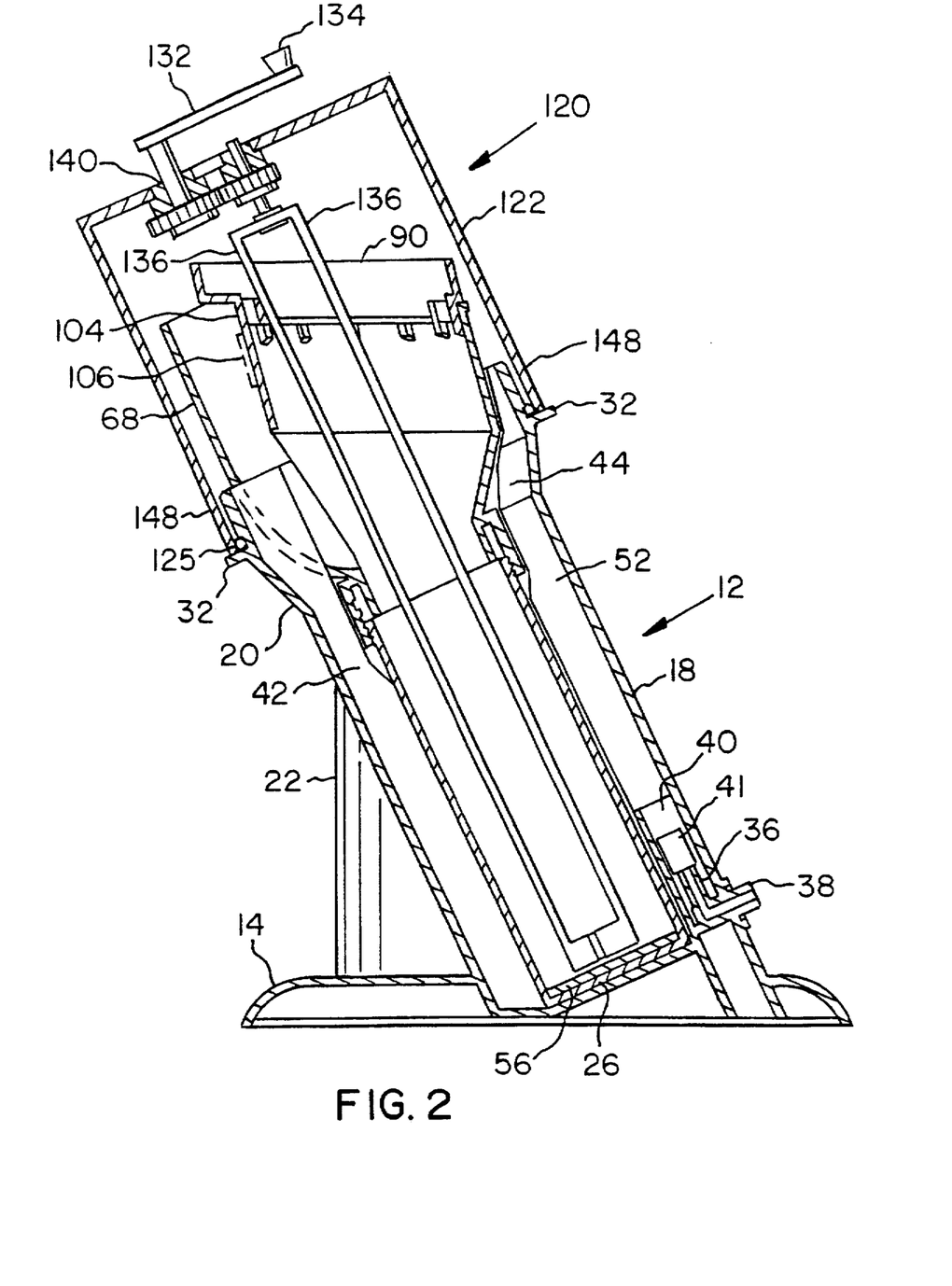
FIG. 2 is a sectional view of the bone cement mixing device of FIG. 1 in assembled form.
Figures 3, 4, 5:
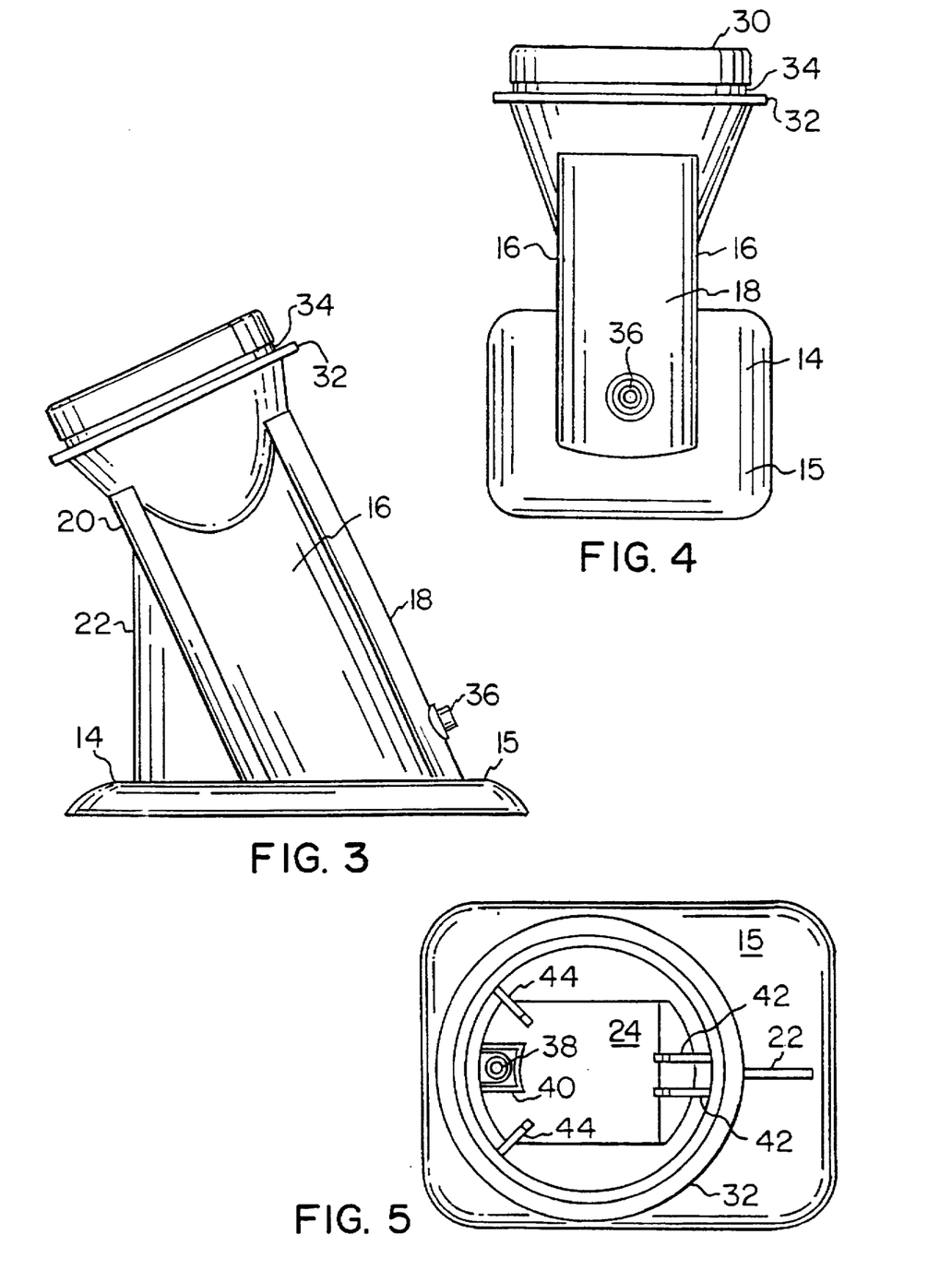
FIG. 3 is a side view of a bone cement housing.
FIG. 4 is a frontal view of the housing shown in FIG. 3.
FIG. 5 is a plan view of the housing shown in FIGS. 3 and 4.

A bone cement mixing device of the present invention is generally designated 10 in FIGS. 1, 2, 20 and 21. A first embodiment of mixing device 10 is shown in FIGS. 1 and 2. Mixing device 10 includes a housing 12 attached to a substantially planar base 14. As shown in FIGS. 1–5, housing 12 includes a pair of oppositely spaced, substantially parallel sidewalls 16, a front wall 18 and a rear wall 20. A substantially planar, vertical support member 22 extends between rear wall 20 and an upper surface 15 of base 14. Housing 12 further includes an internal chamber 24 having a bottom wall 26 and an upper portion 28 with an open top 30. As shown in FIGS. 3 and 4, a contact surface 32 and a sealing or O-ring groove 34 extend around the external surface of upper portion 28 of housing 12. As shown in FIGS. 1 and 2, a sealing element, such as an O-ring 35, is carried in O-ring groove 34.

Housing 12 includes a vacuum tube attachment fitting 36 located on front wall 18 near bottom wall 26. Attachment fitting 36 defines a passage extending through front wall 18 and in flow communication with a filter cartridge fitting 38 located in a filter cartridge enclosure 40 in internal chamber 24. A filter cartridge 41 is attached to cartridge fitting 38. As shown in FIGS. 1 and 5, housing 12 further includes a pair of holding elements 42 spaced apart from each other and extending substantially longitudinally from top 30 to bottom wall 26 of internal chamber 24. Housing 12 further includes a pair of spacing elements 44 located opposite holding elements 42 and extending from open top 30 to bottom wall 26 of internal chamber 24. Housing 12 and base 14 are preferably made of molded plastic.

As shown in FIG. 1, a longitudinal axis L of internal chamber 24 is inclined at an angle Z from a vertical axis V. Angle Z is preferably between 10° to 45°, and in the first embodiment of device 10, is more preferably about 25°.

As shown in FIGS. 1 and 2 and as discussed hereinbelow, mixing device 10 includes a hollow, cylindrical syringe cartridge 50 having a sidewall 52, a bottom closed by a slidable piston 56, an open top 58 and a set of engagement members, such as external threads 60. syringe cartridge 50 is configured to fit within internal chamber 24 of housing 12. The bottom of cartridge 50 rests on bottom wall 26 of internal chamber 24 and sidewall 52 of cartridge 50 is positioned between holding elements 42 and spacing elements 44.

Figure 6:
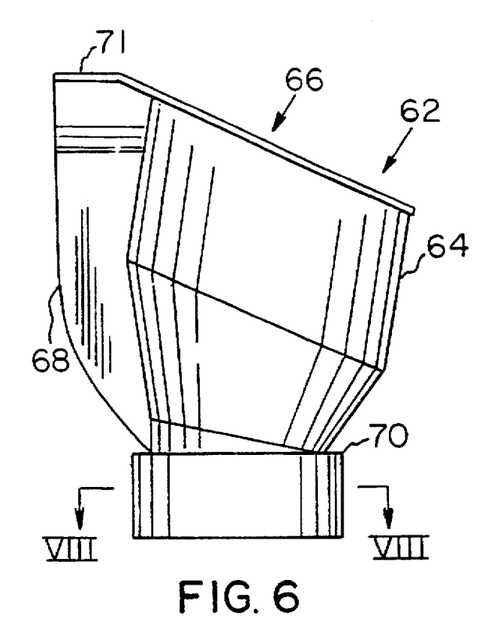
FIG. 6 is a side view of a funnel assembly.
Figure 7:
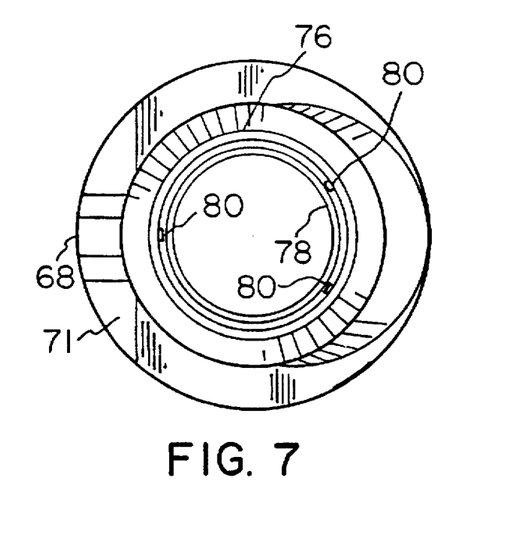
FIG. 7 is a bottom view of the funnel assembly shown in FIG. 6.
Figure 8:
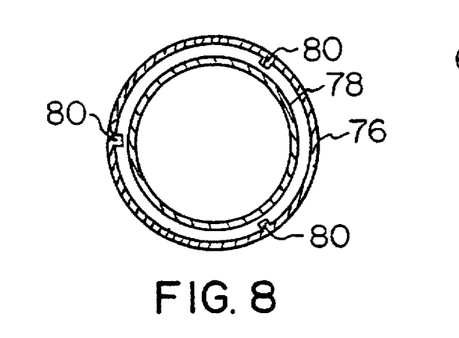
FIG. 8 is a sectional view of the funnel assembly of FIG. 6 taken along the line VIII—VIII.
Figure 9:
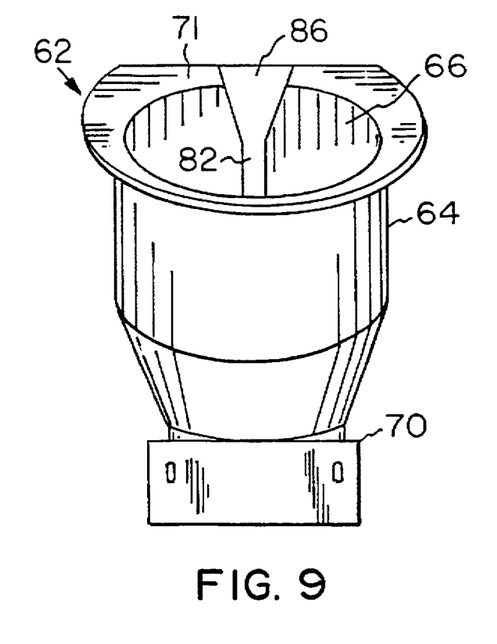
FIG. 9 is a frontal view of the funnel assembly of FIG. 6.
Figure 10:
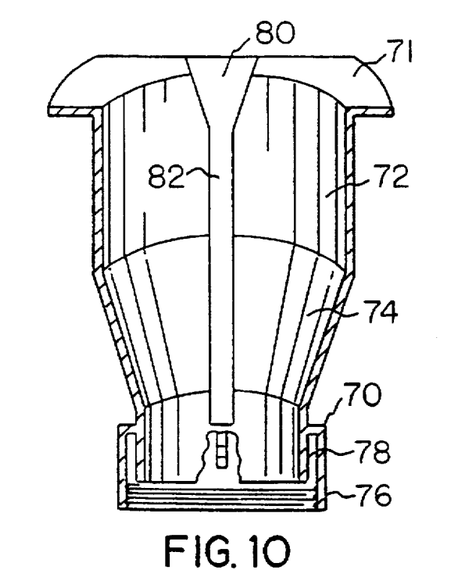
FIG. 10 is a sectional view of the funnel assembly shown in FIG. 9.
Figure 11:
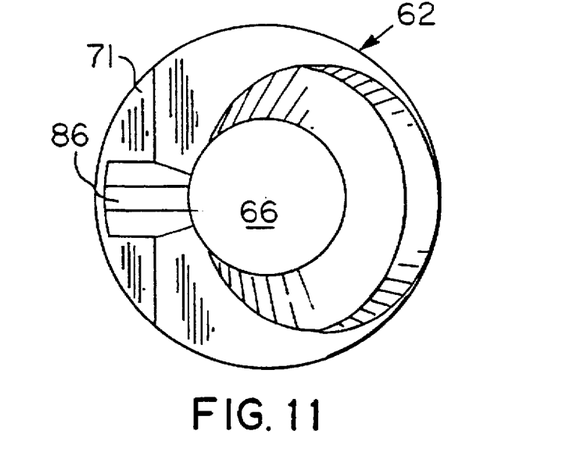
FIG. 11 is a plan view of the funnel assembly shown in FIG. 6.
Figure 12:
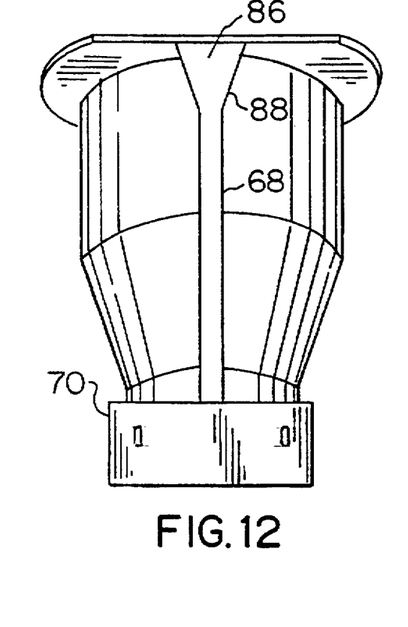
FIG. 12 is a rear view of the funnel assembly shown in FIG. 5.

Mixing device 10 further includes a funnel assembly 62. As shown in FIGS. 1, 6, 9 and 10, funnel assembly 62 includes a sidewall 64, an open top 66, a sidewall projection 68 and a bottom portion 70. A lip portion 71 is located above sidewall projection 68 adjacent open top 66. Funnel assembly 62 further includes an upper main chamber 72 and a throat 74. Throat 74 may be inclined with respect to main chamber 72. As shown in FIGS. 7 and 8, bottom portion 70 includes an annular outer wall 76 and an annular inner wall 78. A plurality of engagement elements 80 are located on outer wall 76 and are configured to engage threads 60 on syringe cartridge 50. As shown in FIGS. 1 and 9-11, sidewall projection 68 includes a fluid channel 82 having a fluid opening 86. Fluid channel 82 extends through main chamber 72 and throat 74. As shown in FIGS. 10 and 12, an upper portion 88 of sidewall projection 68 is wider than the remainder of sidewall projection 68. As shown in FIGS. 1 and 6, top 66 of funnel assembly 62 is chamfered to be substantially horizontal when funnel assembly 62 is inserted into housing 12. Funnel assembly 62 is preferably made of molded plastic.

Figure 13:
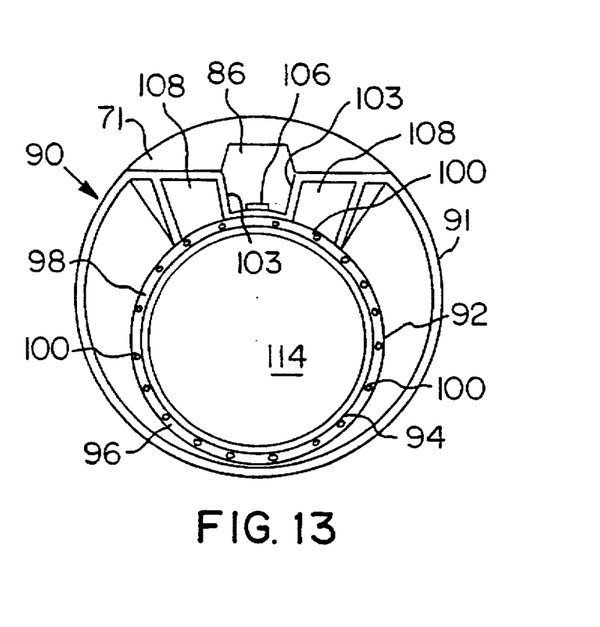
FIG. 13 is a plan, sectional view of a drip ring taken along the line XIII—XIII of FIG. 1 resting on the funnel assembly.

As shown in FIG. 1, an optional drip ring 90 may be carried by funnel assembly 62. If drip ring 90 is present, drip ring 90 is preferably attached near top 66 of funnel assembly 62 by, for example, ultrasonic welding. As shown in FIGS. 1, 2 and 13-15, drip ring 90 includes a sidewall 91, a bottom 93, an annular outer wall 92 and an annular inner wall 94. Outer wall 92 and inner wall 94 define an annular passage 96 having a bottom wall 98. A plurality of holes 100 are located in bottom wall 98 with a hollow drip sleeve 102 located below each hole 100 and in fluid communication with annular passage 96. As shown in FIG. 13, drip ring 90 includes a notched portion 103 such that when drip ring 90 is attached to funnel assembly 62, fluid opening 86 is not obstructed.

Figure 14:
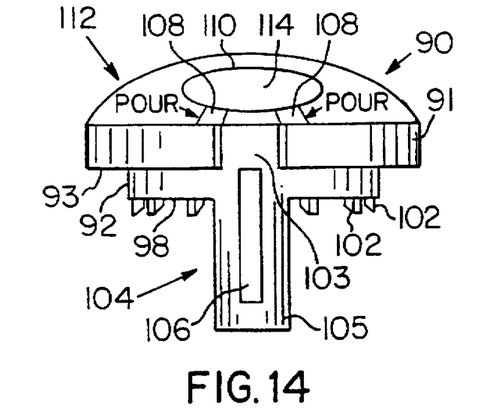
FIG. 14 is a rear view of the drip ring shown in FIG. 13.
Figure 15:
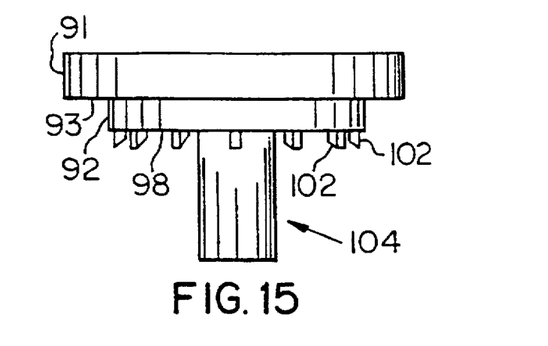
FIG. 15 is a front view of the drip ring shown in FIG. 14.

As shown in FIGS. 14 and 15, drip ring 90 further includes a cover member 104 depending at an angle from drip ring 90. Cover member 104 lies across fluid channel 82 in main chamber 72. A rear surface 105 of cover member 104 includes a thick portion 106 configured to engage the upper portion of fluid channel 82 when drip ring 90 is engaged with funnel assembly 62, as shown in FIG. 2. Drip ring 90 further includes liquid orifices 108 in flow communication with annular passage 96. As shown in FIG. 14, drip ring 90 may further include a cover 110 having instruction indicia 112 printed on an upper surface thereof. A central opening 114 extends through drip ring 90. While in the above description cover member 104 is attached to drip ring 90, a drip ring without a cover member may be used, but this is not preferred.

As shown in FIGS. 1, 2, 18 and 19, mixing device 10 further includes a cap 120 having a sidewall 122, an open bottom 124 having an inside chamfered edge 125, and a closed top 126. Cap 120 supports a manually operated mixer assembly 128 having a two-gear mixer drive 130. A crank arm 132 having a knob 134 actuates mixer drive 130 to rotate a pair of stirrer elements 136 about a mixing axis M.

Figure 18:
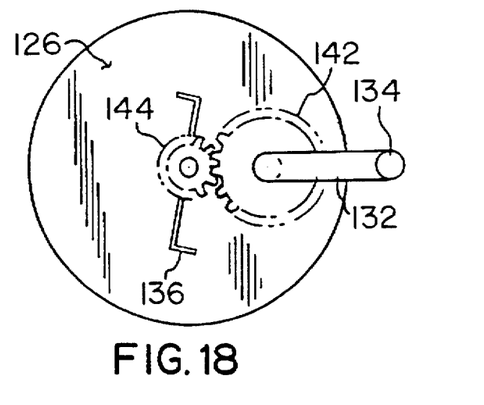
FIG. 18 is a plan view of a top of a cap shown in FIG. 2.
Figure 19:
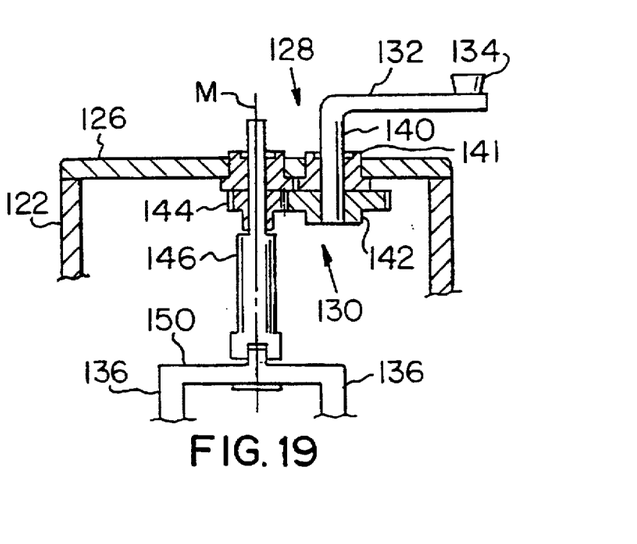
FIG. 19 is a side, sectional view of a mixer assembly.

As shown in FIGS. 18 and 19, mixer drive 130 includes an input shaft 140 extending through a first bushing 141 in top 126 of cap 120 and engaging a first gear 142. Crank arm 132 is attached to the upper end of input shaft 140. Mixer drive 130 further includes a second gear 144 which engages first gear 142 and which is carried on an output shaft 146 extending through a second bushing 147 in top 126. Stirrer elements 136 depend from output shaft 146. First gear 142 is larger than second gear 144 to produce a speed-up gearing factor of about 2.5.

Figure 16:
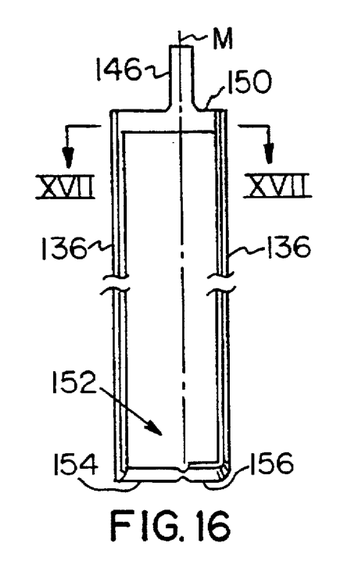
FIG. 16 is a front view of a pair of stirrer elements.
Figure 17:
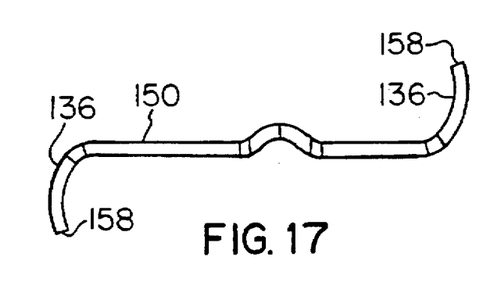
FIG. 17 is a sectional view of the stirrer elements of FIG. 16 taken along the line XVII—XVII.

As shown in FIGS. 16-19, mixer assembly 128 includes a pair of stirrer elements 136 extending substantially parallel to the mixing axis M. Stirrer elements 136 may be spaced an equal distance to either side of axis M, as shown in FIG. 1, or may be asymmetrically positioned, as shown in FIGS. 16 and 17. Stirrer elements 136 are attached to output shaft 146 by an upper arm 150. The lower ends of stirrer elements 136 are joined by a cross arm 152. Cross arm 152 includes a pair of angled mixing blades 154, 156 with the leading edges of the two mixing blades 154, 156 facing in opposite directions.

As shown in FIG. 17, stirrer elements 136 are curved in cross-section such that leading edges 158 of stirrer elements 136 are substantially tangential to the direction of travel during rotation. As can be seen, the angle of incidence increases toward the trailing edges of elements 136. This configuration produces a high angle of throw and greatly reduces the time required to mix the bone cement.

In the assembled form as shown in FIG. 2, 0-ring 148 abuts chamfered edge 125 of cap 120 to tightly seal cap 120 to housing 12. Further, stirrer elements 136 extend through central opening 114 in drip ring 90 and through funnel assembly 62 into syringe cartridge 50.

Figure 20:
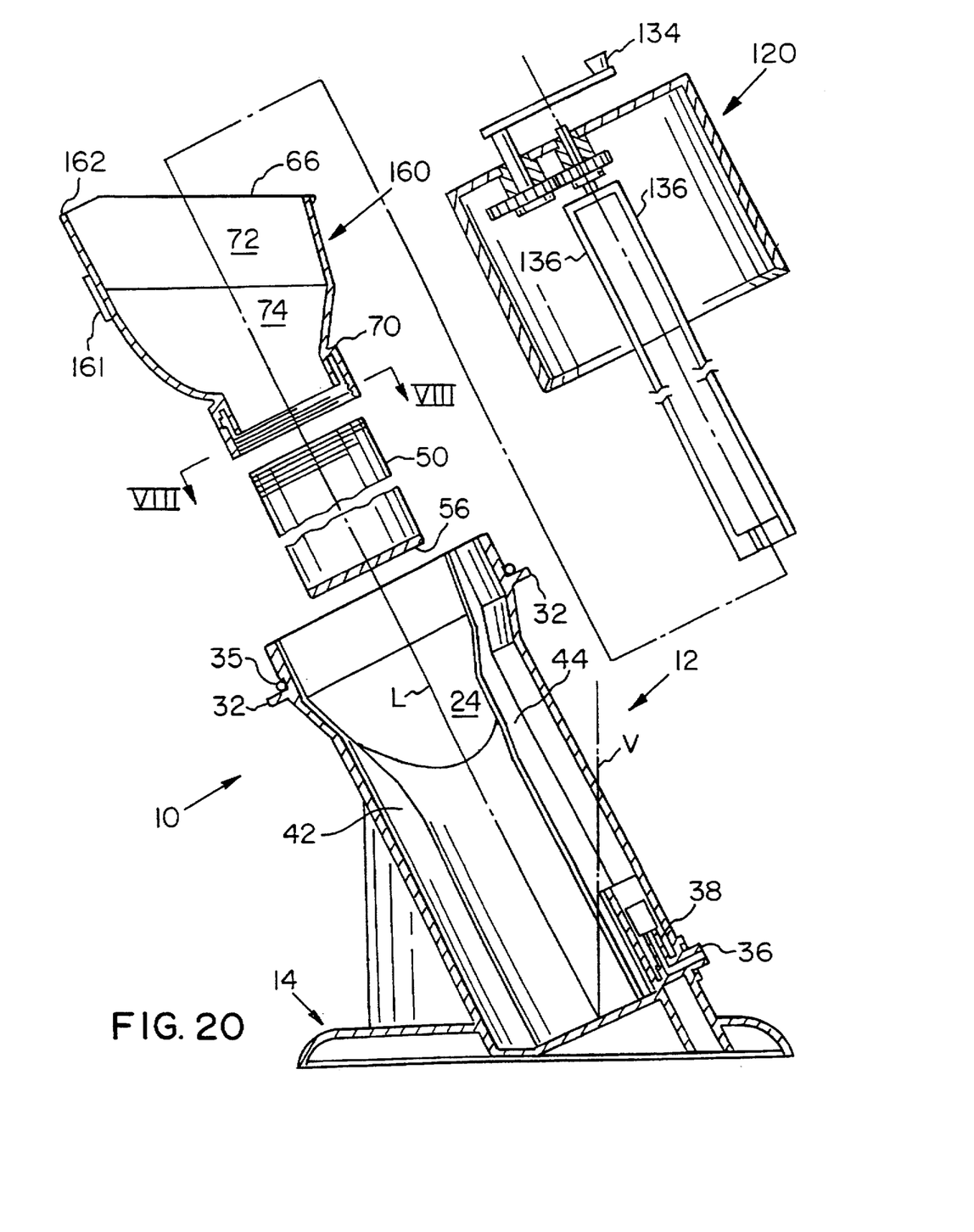
FIG. 20 is an expanded, sectional view of a second embodiment of the bone cement mixing device.
Figure 21:
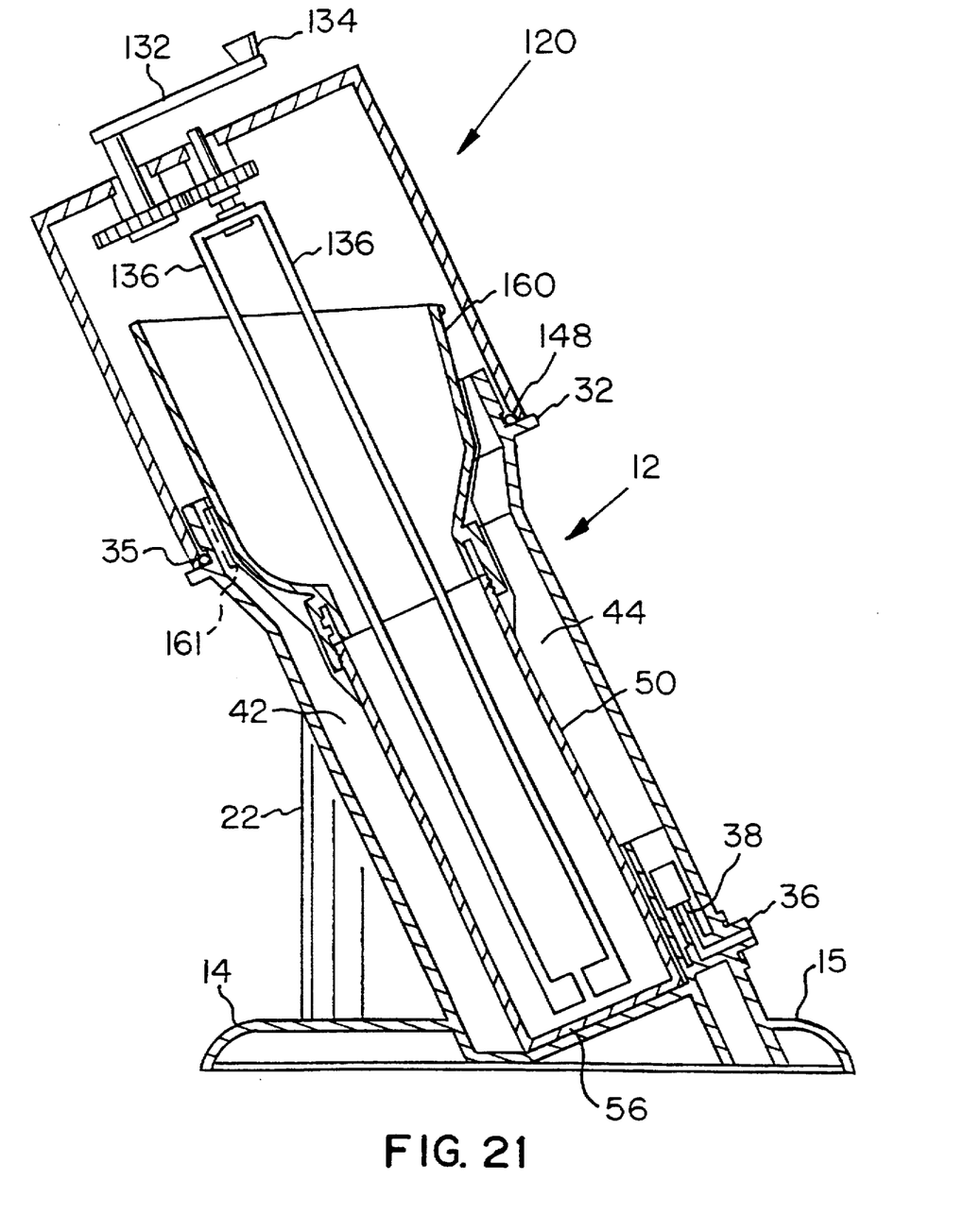
FIG. 21 is a sectional view of the bone cement mixing device of FIG. 20 in assembled form.

FIGS. 20 and 21 show a second embodiment of mixing device 10 having a simplified funnel assembly 160. Funnel assembly 160 is similar to funnel assembly 62 except as follows. Firstly, as shown in FIGS. 20 and 21, funnel assembly 160 does not include a fluid channel 82 as contained in funnel assembly 62. Secondly, an external tab 161 is provided which, by contacting one of the holding elements 42, will serve to prevent rotation of funnel assembly 160 during stirring. Thirdly, the upper portions of holding elements 42 are narrowed to conform to the shape of funnel assembly 160. Also with this embodiment, the inclination of longitudinal axis L of internal chamber 24 remains preferably between 10° and 45°, but is more preferably about 40°. Greater inclination of internal chamber 24 is required for reliable operation of the second embodiment since no fluid channel 82 is provided.

Figure 23:
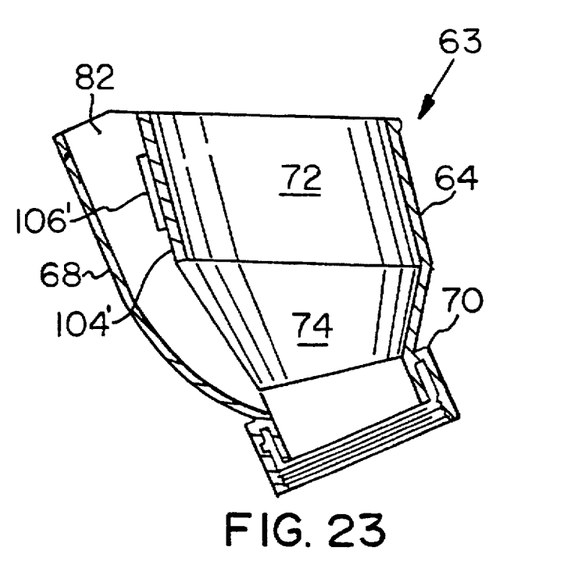
FIG. 23 is a sectional view of an alternative embodiment of the funnel assembly.

FIG. 23 shows an alternative funnel assembly 63 for use with mixing device 10 when drip ring 90 is not used. Funnel assembly 63 is similar to funnel assembly 62 shown in FIGS. 1 and 2 but further includes a cover member 104' overlying fluid channel 82 in main chamber 72. Cover member 104' includes a thick portion 106' which extends slightly into fluid channel 82. Cover member 104' prevents powder poured into funnel assembly 63 from clogging fluid channel 82. Cover member 104' is preferably held in place by ultrasonic welding.

Operation of mixing device 10 will now be described.

First, operation of the first embodiment of mixing device 10 shown in FIGS. 1 and 2 without the optional drip ring 90 will be discussed. Bottom portion 70 of funnel assembly 62 is threaded onto open top 58 of syringe cartridge 50 such that engagement elements 80 engage threads 60 on cartridge 50. The joined cartridge 50 and funnel assembly 62 are then inserted into open top 30 of housing 12 and into internal chamber 24. Sidewall projection 68 is held between holding elements 42 to prevent funnel assembly 62 and syringe cartridge 50 from rotating during operation of mixing device 10. The required amounts of dry polymer powder are poured through open top 66 of funnel assembly 62 into syringe cartridge 50. The inclination of syringe cartridge 50 decreases the billowing of powder as it is poured since the powder can slide down the inclined, lower portion of sidewall 52 of cartridge 50 instead of dropping vertically onto the bottom of a vertical chamber. When two doses of powder are dispensed, the column of unwetted powder may extend into bottom portion 70 and throat 74 of funnel assembly 62. Where three doses are dispensed, unwetted powder will extend further upwards, filling most of funnel assembly 62.

Monomer liquid is then poured into fluid opening 86 of funnel assembly 62 and flows through fluid channel 82 and along the lower portion of sidewall 52 of syringe cartridge 50. The inclination of syringe cartridge 50 in housing 12 greatly reduces the flow of monomer liquid transversely across the interior of syringe cartridge 50 and allows for the monomer liquid to flow preferentially along the lower portion of sidewall 52 of cartridge 50 toward piston 56. Fluid channel 82 along the lower side of funnel assembly 62 provides a path for liquid monomer where it will not flow significantly into the powder at the level of the funnel. Consequently, at all levels in funnel assembly 62 and syringe cartridge 50, a portion of the cross-section of powder will remain unwetted as monomer flows downward. Air displaced by the flow of monomer toward the bottom of cartridge 50 can therefore escape by filtering upward through a column of unwetted powder along the interior and upper sidewall 52 of syringe cartridge 50 and funnel assembly 62. If more than two doses of bone cement are being mixed, only the first two doses of monomer liquid are poured into fluid opening 86. The final dose of monomer is poured so as to distribute it along an inner circumference of the upper main chamber 72 of the funnel assembly 62. This will ensure adequate wetting of powder in the upper part of funnel assembly 62 and will wash powder from the sides of funnel assembly 62 into syringe cartridge 50. After dispensing of polymer and monomer is complete, cap 120 with attached mixer assembly 128 is placed onto housing 12 so as to sealably close housing 12 with stirrer elements 136 extending into syringe cartridge 50 as shown in FIG. 2. A vacuum is applied inside housing 12 through vacuum attachment fitting 36. The polymer and monomer are mixed by turning crank arm 132 clockwise at a preferred rate of 1.5 to 2 Hz until adequate mixing has been accomplished. Turning crank arm 132 clockwise causes stirrer elements 136 to rotate counterclockwise which applies a counterclockwise torque to the bone cement in syringe cartridge 50 thus helping to keep syringe cartridge 50 tightly threaded onto funnel assembly 62. The structure of stirrer elements 136 reduces the stirring time required to produce bone cement to about 45 seconds with the present embodiment.

After mixing, the vacuum source is turned off and cap 120 is removed from housing 12. Funnel assembly 62 and attached syringe cartridge 50 containing the freshly mixed bone cement are removed from internal chamber 24 and syringe cartridge 50 is unthreaded from funnel assembly 62. A nozzle is then attached to syringe cartridge 50 which is then placed in a bone cement applicator gun for delivery of the bone cement to an implant site. The bone cement rapidly hardens to form a strong joint securing a prosthetic element in place.

Figure 22:
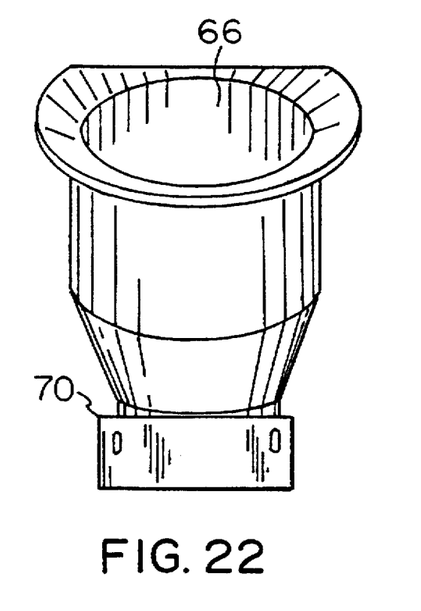
FIG. 22 is a front view of a second embodiment of the funnel assembly.

Operation of mixing device 10 with alternative funnel assembly 63 shown in FIG. 22 is the same as described above with respect to operation using funnel assembly 62. However, cover member 104' ensures that powder cannot become packed into the upper part of fluid channel 82 so as to clog fluid channel 82. Cover member 104' also prevents monomer liquid from flowing into the powder at the upper level of funnel assembly 63 thus helping to maintain the column of unwetted powder along the interior upper portion of sidewall 52 of syringe cartridge 50 to allow a flow path for the escape of air from the interior of syringe cartridge 50.

Operation of the first embodiment of mixing device 10 shown in FIGS. 1 and 2 with an optional drip ring 90 is as follows. Drip ring 90 rests in open top 66 of funnel assembly 62 with cover member 104 overlying fluid channel 82 in main chamber 72, as shown in FIG. 2. Preferably, drip ring 90 is secured in this position by ultrasonic welding or the like. Cartridge 50 is threaded onto bottom portion 70 of funnel assembly 62 and inserted into internal chamber 24 as discussed above. The polymer powder is poured through central opening 114 of drip ring 90, through funnel assembly 62 and into cartridge 50. If two or fewer doses of bone cement are to be mixed, all doses of monomer liquid are preferably poured into fluid opening 86 of funnel assembly 62. Cover member 104 ensures that powder cannot become packed into the upper part of fluid channel 82 of funnel assembly 62 so as to clog fluid channel 82. If three doses of bone cement are to be mixed, two doses of monomer liquid are poured into fluid opening 86. The third dose of monomer liquid is poured into one of orifices 108 and flows into annular passage 96. The monomer in annular passage 96 then drips through holes 100 and drip sleeves 102 onto the top of the polymer powder. Cap 120 is then placed on housing 12 and the polymer and monomer mixed as described above. Use of drip ring 90 provides complete repeatability of monomer distribution into the upper part of funnel assembly 62, whereas the technique used without it is more subject to operator variability.

Operation of the second embodiment of mixing device 10 shown in FIGS. 19 and 20 will now be described. Cartridge 50 is threaded onto bottom 70, and funnel assembly 160 and cartridge 50 are inserted into internal chamber 24 of housing 12. The required amount of polymer powder is poured into open top 66 of funnel assembly 160 and into cartridge 50. The required amount of monomer is then poured into open top 66 of funnel assembly 160 at a lower edge 162 and flows through funnel assembly 62 and into syringe cartridge 50. Cap 120 is then placed on housing 12 and the polymer and monomer mixed as described above.

While embodiments of the invention have been described in detail herein, it will be appreciated by those skilled in the art that various modifications and alternatives to the embodiments could be developed in light of the overall teachings of the disclosure. Accordingly, the particular arrangements and procedures are illustrative only and are not limiting as to the scope of the invention which is to be given the full breadth of the appended claims and any and all equivalents thereof.

I claim:

1. A device for mixing a liquid monomer with a polymer powder to form a bone cement, the device comprising:
   a housing having an open top;
   a non-rotatable internal chamber located in said housing, wherein said internal chamber is inclined at an angle from a vertical axis;
   a syringe cartridge configured to be removably and non-rotatably received in said internal chamber;
   a cap configured to fit over said open top of said housing to sealably close said housing; and
   a mixer assembly having at least one stirrer element configured to extend into said syringe cartridge in said internal chamber.

2. The device as claimed in claim 1, wherein said syringe cartridge has a sidewall, a bottom closed by a slidable piston and a set of engagement members.

3. The device as claimed in claim 1, wherein said internal chamber is inclined at an angle between 10° to 45° from the vertical axis.

4. The device as claimed in claim 1, further including a base, wherein said housing is attached to said base.

5. The device as claimed in claim 4, wherein said device includes a support member positioned between said base and said housing.

6. The device as claimed in claim 1, wherein said housing includes a contact surface extending from said housing and configured to support said cap when said cap is placed on said housing.

7. The device as claimed in claim 1, wherein said housing includes a sealing groove located in said housing and a sealing element carried in said sealing groove, said sealing element configured to abut said cap to sealably close said housing.

8. The device as claimed in claim 1, wherein said internal chamber includes a pair of spaced apart holding elements which project radially inwardly and are configured to abut said syringe cartridge and to prevent rotation of said syringe cartridge is received in said internal chamber.

9. The device as claimed in claim 1, wherein said internal chamber includes at least one spacing element protecting radially inward and configured to abut said syringe cartridge to center said syringe cartridge in said internal chamber.

10. The device as claimed in claim 1, wherein said housing includes a front wall, a rear wall and a pair of substantially planar sidewalls.

11. The device as claimed in claim 1, further including a vacuum passage extending into said internal chamber and a vacuum attachment fitting in flow communication with said vacuum passage.

12. The device as claimed in claim 11, further including a filter cartridge fitting located in said interior chamber and in flow communication with said vacuum passage.

13. The device as claimed in claim 1, wherein an axis of rotation of said at least one stirrer element is substantially parallel to a longitudinal axis of said internal chamber.

14. The device as claimed in claim 1, further including a funnel assembly having a sidewall, a top and a bottom portion, wherein said funnel assembly is in flow communication with said syringe cartridge of said housing.

15. The device as claimed in claim 14, wherein said funnel includes an upper main chamber and a throat.

16. The device as claimed in claim 11 wherein said syringe container has engagement members and wherein said bottom portion of said funnel assembly includes engagement elements configured to engage said engagement members of said syringe container.

17. The device as claimed in claim 11, including a pair of spaced apart holding elements located in said internal chamber, wherein said funnel assembly includes a tab extending from said sidewall of said funnel assembly, with said tab configured to engage said holding elements to prevent rotation of said funnel assembly during mixing.

18. The device as claimed in claim 11, wherein said internal chamber is inclined at an angle of about 40° from the vertical axis.

19. The device as claimed in claim 1, wherein said cap has a sidewall and a chamfered edge located on a bottom of said sidewall.

20. The device as claimed in claim 19, wherein said mixer assembly is carried on said cap.

21. A device for mixing bone cement, comprising:
   a housing having an open top;
   an internal chamber located in said housing, wherein said internal chamber is inclined at an angle from a vertical axis;
   a cap configured to fit over said open top of said housing to sealably close said housing;
   a mixer assembly having at least one stirrer element configured to extend into said internal chamber; and
   a funnel assembly having a sidewall, a top and a bottom portion,
   wherein said funnel assembly is in flow communication with said internal chamber of said housing, and
   wherein said funnel assembly further includes a fluid channel located in said sidewall of said funnel assembly and configured to direct at least a portion of the monomer liquid through said funnel assembly.

22. The device as claimed in claim 21, further including a cover member, wherein said cover member is configured to cover at least a portion of said fluid channel in said funnel assembly.

23. The device as claimed in claim 21, further including a drip ring carried on said funnel assembly and in flow communication with said funnel assembly.

24. The device as claimed in claim 23, wherein said drip ring includes at least one orifice and an annular passage in flow communication with said at least one orifice, said annular passage having a bottom wall with at least one hole located in said bottom wall.

25. The device as claimed in claim 24, wherein said drip ring further includes a cover member depending therefrom, wherein said cover member is configured to cover at least a portion of said fluid channel in said funnel assembly.

26. The device as claimed in claim 25, wherein said drip ring further includes a notched portion configured to align with a fluid opening of said funnel assembly when said drip ring is carried on said funnel assembly.

27. The device as claimed in claim 21, wherein said internal chamber is inclined at an angle of about 25° from the vertical axis.

28. A device for mixing bone cement, comprising:
   a housing having an open top;
   an internal chamber located in said housing, wherein said internal chamber is inclined at an angle from a vertical axis;
   a cap configured to fit over said open top of said housing to sealably close said housing;

a mixer assembly having at least one stirrer element configured to extend into said internal chamber; and a funnel assembly having a sidewall, a top and a bottom portion, wherein said funnel assembly is in flow communication with said internal chamber of said housing, wherein said funnel includes an upper main chamber and a throat, and wherein said funnel assembly includes a sidewall projection, a fluid opening in said top of said funnel assembly and a fluid channel extending from said fluid opening, through said sidewall projection, to said throat.

29. A device for mixing a liquid monomer with a polymer powder to form a bone cement, the device comprising:

a hollow housing having an open top;

a non-rotatable internal chamber located in said housing, wherein said internal chamber is inclined at an angle between 10° and 45° from a vertical axis;

a non-rotatable syringe cartridge having a sidewall, a bottom closed by a slidable piston and a set of engagement members, wherein said syringe cartridge is configured to be removably and non-rotatably received in said internal chamber;

a vacuum passage extending into said internal chamber of said housing;

a vacuum attachment fitting in flow communication with said vacuum passage;

a funnel assembly having a sidewall, a top and a bottom portion, wherein said bottom portion includes engagement elements configured to engage said engagement members of said syringe cartridge, and wherein said funnel assembly is in flow communication with an interior of said syringe cartridge;

a cap configured to fit over said open top of said housing to sealably close said housing; and a rotary mixer having at least one stirrer element configured to extend into said interior of said syringe cartridge.

30. A device for mixing bone cement, comprising:

a hollow housing having an open top;

an internal chamber located in said housing, wherein said internal chamber is inclined at an angle between 10° and 45° from a vertical axis;

a syringe cartridge having a sidewall, a bottom closed by a slidable piston and a set of engagement members, wherein said syringe cartridge is configured to extend into said internal chamber;

a vacuum passage extending into said internal chamber of said housing;

a vacuum attachment fitting in flow communication with said vacuum passage;

a funnel assembly having a sidewall, a top and a bottom portion, wherein said bottom portion includes engagement elements configured to engage said engagement members of said syringe cartridge, and wherein said funnel assembly is in flow communication with an interior of said syringe cartridge;

a cap configured to fit over said open top of said housing to sealably close said housing; and a rotary mixer having at least one stirrer element configured to extend into said interior of said syringe cartridge, wherein said funnel assembly includes a fluid opening in said top of said funnel assembly and a fluid channel extending from said fluid opening through said funnel assembly sidewall.

31. The device as claimed in claim 30, further including a drip ring carried on said funnel assembly, wherein said drip ring includes at least one fluid orifice and an annular passage in flow communication with said at least one orifice, said annular passage having a bottom wall and at least one hole located in said bottom wall of said annular passage and in flow communication with an interior of said funnel assembly.

32. The device as claimed in claim 30, further including a cover member configured to cover at least a portion of said fluid channel in said funnel assembly.

33. A device for mixing bone cement, comprising:

a housing having a front wall, a rear wall, a pair of substantially planar sidewalls and an open top;

an internal chamber located in said housing, wherein said internal chamber is inclined at an angle of between 10° to 45° from a vertical axis;

a syringe cartridge having a sidewall, a bottom closed by a slidable piston and a set of engagement members, wherein said syringe cartridge is configured to fit into said internal chamber;

a vacuum passage extending through said housing into said internal chamber;

a vacuum attachment fitting in flow communication with said vacuum passage;

a rotary mixer having at least one stirrer element configured to extend into an interior of said syringe cartridge;

a funnel assembly having a top and a bottom portion, wherein said funnel assembly is located above and in flow communication with said interior of said syringe cartridge, wherein said funnel assembly includes an upper main chamber, a throat and a sidewall projection, and wherein said bottom portion of said funnel assembly includes engagement elements configured to engage said engagement members of said syringe cartridge;

a fluid opening in said top of said funnel assembly;

a fluid channel, wherein said fluid channel extends from said fluid opening in said top of said funnel assembly through said sidewall projection to said throat;

a drip ring located above said funnel assembly, wherein said drip ring includes an annular passage having a bottom, at least one orifice in flow communication with said annular passage, and at least one hole located in said bottom of said annular passage and in flow communication with said main chamber;

a cover member configured to cover at least a portion of said fluid channel in said main chamber; and a cap configured to fit over said open top of said housing to sealably close said housing.

34. A method of mixing a bone cement liquid and a bone cement powder to form a mixed bone cement, comprising the steps of:

placing the bone cement powder into an inclined syringe cartridge;

introducing the bone cement liquid into said inclined syringe cartridge; and mixing said bone cement liquid and bone cement powder to form mixed bone cement.

35. The method of claim 34, wherein said step of placing bone cement powder into said inclined syringe cartridge includes the step of pouring bone cement powder through a funnel assembly into said inclined syringe cartridge, wherein said funnel assembly is located above said syringe cartridge.

36. The method as claimed in claim 35, wherein said step of introducing bone cement liquid into said inclined syringe cartridge includes the step of pouring at least a portion of said bone cement liquid into said funnel assembly near a lower edge of said funnel assembly.

37. A method of mixing bone cement, comprising the steps of:

placing bone cement powder into an inclined chamber;

introducing bone cement liquid into said chamber; and mixing said bone cement liquid and bone cement powder to form mixed bone cement, wherein said step of placing bone cement powder into said inclined chamber includes the step of pouring bone cement Powder through a funnel assembly into a syringe container, wherein said funnel assembly is located above said syringe container wherein said step of introducing the bone cement liquid into said inclined syringe cartridge includes the step of pouring at least a portion of said bone cement liquid into a fluid channel located in a sidewall of said funnel assembly.

38. The method as claimed in claim 37, wherein said step of introducing bone cement liquid into said inclined syringe cartridge includes the step of pouring at least a portion of said bone cement liquid into a drip ring located above and in flow communication with said funnel assembly.

39. A bone cement mixing sub-assembly for co-acting with a bone cement mixing housing having an inclined, non-rotatable internal chamber, the bone cement mixing sub-assembly adapted to mix a liquid monomer with a polymer powder to form a bone cement, the sub-assembly comprising:

a syringe cartridge configured to be removably and non-rotatably received in the internal chamber;

a cap configured to fit over an open top of the housing to sealably close the housing; and a mixer assembly having at least one stirrer element configured to extend into the syringe cartridge in the internal chamber.

40. The sub-assembly as claimed in claim 39, further including a funnel assembly having a side wall, a top and a bottom portion, wherein the funnel assembly is configured to engage the housing and to be in flow communication with the syringe cartridge.

41. The sub-assembly as claimed in claim 40, wherein the funnel assembly includes a tab extending from the side wall of the funnel assembly, the tab configured to engage holding elements in the internal chamber to prevent rotation of the funnel assembly during mixing.

42. The sub-assembly as claimed in claim 41, wherein the funnel assembly further includes a fluid channel located in the side wall of the funnel assembly and configured to direct bone cement liquid into the syringe cartridge.

43. The sub-assembly as claimed in claim 42, further including a cover member, wherein the cover member is configured to cover at least a portion of the fluid channel in the funnel assembly.

44. The sub-assembly as claimed in claim 42, further including a drip ring carried on the funnel assembly and configured to be in flow communication with the funnel assembly.

45. The sub-assembly as claimed in claim 44, wherein the drip ring includes at least one orifice and an annular passage in flow communication with the at least one orifice, the annular passage having a bottom wall with at least one hole located in the bottom wall.

46. The sub-assembly as claimed in claim 45, wherein the drip ring further includes a cover member depending therefrom, wherein the cover member is configured to cover at least a portion of the fluid channel in the fluid assembly.

47. The sub-assembly as claimed in claim 40, wherein the funnel assembly includes a side wall projection, a fluid opening in the top of the funnel assembly and a fluid channel extending from the fluid opening through the side wall projection.

* * * * *

UNITED STATES PATENT AND TRADEMARK OFFICE
CERTIFICATE OF CORRECTION

PATENT NO. : 5,797,678
DATED : August 25, 1998
INVENTOR(S) : William M. Murray

It is certified that error appears in the above-identified patent and that said Letters Patent is hereby corrected as shown below:

Claim 16 Column 10 Line 1 "in claim 11" should read --in claim 14--.

Claim 17 Column 10 Line 6 "in claim 11" should read --in claim 14--.

Claim 18 Column 10 Line 12 "in claim 11" should read --in claim 14--.

Claim 30 Column 11 Line 47 after "axis" delete colon and insert semicolon --;--.

Claim 42 Column 14 Line 14 "in claim 41" should read --in claim 40--.

Signed and Sealed this

Eighth Day of December, 1998

*Attest:*

*Attesting Officer*

BRUCE LEHMAN

*Commissioner of Patents and Trademarks*